United States Patent [19]

Lee et al.

[11] Patent Number: 5,413,795
[45] Date of Patent: May 9, 1995

[54] TCMTB ON A SOLID CARRIER IN POWDERED FORM, METHOD OF MANUFACTURE AND METHOD OF USE

[75] Inventors: James C. Lee; Mohan D. Karve, both of Memphis, Tenn.

[73] Assignee: Buckman Laboratories, International, Inc., Memphis, Tenn.

[21] Appl. No.: 929,361

[22] Filed: Aug. 14, 1992

[51] Int. Cl.$^6$ .............................................. A61K 9/14
[52] U.S. Cl. ................................. 424/489; 424/404; 424/405; 424/406
[58] Field of Search .................. 424/489; 435/254; 514/367

[56] References Cited

U.S. PATENT DOCUMENTS

| | | | |
|---|---|---|---|
| 3,520,976 | 7/1970 | Buckman et al. | 424/270 |
| 4,293,559 | 10/1981 | Buckman et al. | 424/270 |
| 4,479,961 | 10/1984 | Martin | 424/270 |
| 4,595,691 | 6/1986 | LaMarre et al. | 514/367 |
| 4,839,373 | 6/1989 | Ito et al. | 514/367 |
| 4,866,081 | 9/1989 | Ito et al. | 514/367 |
| 4,915,947 | 4/1990 | Thenard et al. | 424/408 |
| 4,944,892 | 7/1990 | Leathers et al. | 252/92 |
| 4,983,618 | 1/1991 | Pulido et al. | 514/367 |
| 5,013,747 | 5/1991 | Katayama et al. | 514/367 |
| 5,043,090 | 8/1991 | Camp et al. | 252/106 |
| 5,096,824 | 3/1992 | Seifert et al. | 435/254 |

FOREIGN PATENT DOCUMENTS 4-36203  2/1992  Japan .......................... A01N 43/78

OTHER PUBLICATIONS

Chemical Abstracts, vol. 81, No. 3, Abstract No. 10481u (1974).
W. V. Valkenburg, Pesticide Formulations, Chap. 5 (Marcel Dekker, Inc. 1973).
Pesticide Formulations and Applications Systems, K. G. Seymour ed., 1983, pp. 32–44 Literature Search Conducted by Applicants.

*Primary Examiner*—Thurman K. Page
*Assistant Examiner*—William E. Benston, Jr.
*Attorney, Agent, or Firm*—Finnegan, Henderson, Farabow, Garrett and Dunner

[57] ABSTRACT

A composition comprising TCMTB and a solid, preferably inert, carrier. The composition is in a powdered form and can be effective for preventing the growth of microorganisms. A method for preparing this composition comprises mixing the TCMTB with the carrier.

41 Claims, No Drawings

TCMTB ON A SOLID CARRIER IN POWDERED FORM, METHOD OF MANUFACTURE AND METHOD OF USE

This invention relates to a composition comprising 2 (thiocyanomethylthio)-benzothiazole (TCMTB) on a solid, preferably inert, carrier in powdered form, which powdered TCMTB is particularly useful as a pesticide. The invention also relates to a process for the preparation of such compositions of powdered TCMTB, and processes for the use of such powdered TCMTB compositions. More particularly, the invention relates to a process for the preparation of a powdered TCMTB composition, particularly a stable powdered TCMTB composition, formulations containing such a composition and uses of these formulations, particularly as pesticides.

Various physical forms of pesticides are formulated for different reasons. These forms include emulsifiable concentrates (EC), wettable powders (WP), aqueous suspensions (AS) or flowables (F), water dispersible granules (WDG) or dry flowables (DF), granules, solutions (S), microcapsules, microemulsions and dusts. Each of these forms has advantages and disadvantages that are well-known to one skilled in the art.

The compositions of the invention can be used as pesticides, defined herein to include, for example, insecticides, herbicides, rodenticides, fungicides, algaecides, acaricides, molluscicides, nematocides, and plant growth regulators.

Emulsifiable concentrates have been the most popular form of pesticides used in the agricultural industry. Since most pesticides are not water soluble, it has been necessary to find a suitable solvent to dissolve the pesticide and an emulsifier to emulsify the solution. The resulting solution can be diluted with a large amount of water to form a macroemulsion for application, for example, to agricultural products. However, one of the challenges in forming emulsions is that water of different degrees of hardness may be used, and the temperature may differ depending upon the time of day or year of the application.

The thermal stability of a pesticide as a homogeneous dispersion in diluted water is critical for its efficacy. Emulsifiable concentrates are advantageous in that they are easy to manufacture and use, but they can suffer from the disadvantages of flammability, phytotoxicity, environmental pollution and odor problems.

TCMTB is a broad spectrum, effective fungicide which has primarily been used as an emulsifiable concentrate in various industrial applications. Emulsifiable concentrates have generally involved a solvent as a necessary ingredient.

Organic solvents are most commonly used for dissolving TCMTB, since water can cause crystallization of TCMTB at low temperatures. However, the use of an organic solvent can be undesirable for environmental reasons. Moreover, for many uses, the addition of large amounts of solvents or emulsifiers can adversely affect desired properties, such as the tackiness of adhesives.

Certain compositions which are not soluble in industrial solvents are generally applied in the form of wettable powders. Wettable powders are generally produced by applying the pesticides along with a wetting agent and one or more dispersants to a carrier or filler (diluent). The term "carrier" generally refers to materials with high absorptivities, whereas the term "filler" refers to materials having low or medium sorptive capacities.

The materials, which can be used in the present invention as carriers, preferably as inert carriers, for the TCMTB to form powdered TCMTB, can be divided into categories, such as inorganic minerals, botanicals, and synthetics. Generally, these materials can be termed powders, which can encompass particle sizes of 4 mesh or finer (4750 microns or smaller). In particular, powders of a size ranging from 4 to 80 mesh (4750–180 microns) can be called granules and those finer than 80 mesh (180 microns) can be called dusts. A preferred particle size of a dust is at least 85% finer than a 325 mesh (45 microns). The present invention can be carried out without a wetting agent when self-wettable carriers are utilized.

Illustrative minerals of the materials described above which are useful in the present invention as carriers are preferably selected from:
(A) Elements:
  1. sulfur
(B) Silicates:
  1. Clays
    (a) Palygorskite group:
      (1) attapulgite
      (2) sepiolite
      (3) palygorskite
    (b) Kaolinite group
      (1) anauxite
      (2) dickite
      (3) kaolinite
      (4) nacrite
    (c) Montmorillonite group
      (1) beidellite
      (2) montmorillonite
      (3) nontronite
      (4) saponite
    (d) Illite group
      (1) mica
      (2) vermiculite
  2. Pyrophyllite
  3. Talcs
(C) Carbonates:
  1. Calcite
  2. Dolomite
(D) Sulfates:
  1. Gypsum
(E) Oxides:
  1. Calcium:
    (a) Calcium lime
    (b) Magnesium lime
  2. Silicon:
    (a) Diatomire
    (b) Tripolite
(F) Phosphates:
  1. Apatite and
(G) Indeterminate:
  1. Pumice.

Illustrative botanical materials of the materials described above which are useful in the present invention as carriers are preferably selected from:
(A) Citrus pulp
(B) Corn cob
(C) Ground grains
(D) Rice hulls
(E) Soybean
(F) Tobacco
(G) Walnut shell and (H) Wood.

Illustrative synthetic carriers of the materials described above which are useful in the present invention are preferably selected from:

(A) Inorganics:
1. Precipitated hydrated calcium silicate
2. Precipitated calcium carbonate
3. Precipitated hydrated silicon dioxide.

(B) Organic polymers:
1. copolymer of styrene and divinyl benzene
2. cellulose.

Other additives such as anti-caking agents and anti-foaming agents may also be used. Illustrative wetting, dispersing, anti-foam, anti-caking agents and emulsifiers can be found in McCutcheon's publication "Emulsifiers & Detergents, Functional Materials", which is specifically incorporated by reference herein.

The preparation of powdered pesticides, particularly wettable powders, can be divided into three separate steps: (1) pre-blending, e.g., blending powders and/or dusts together, (2) coating, and (3) post-blending. In the context of the present invention, it may not be necessary to use one or both of steps (1) and (3). If used, smaller particles, such as dusts, have the advantage of being able to evenly spread the pesticide over the area to be controlled. However, such smaller particles also have a disadvantage in that they may be blown off of the contact control area. This may be unsuitable for some agricultural applications but may be suitable for other applications, such as preservatives for adhesive and paint.

TCMTB is a heat-sensitive compound. Pure TCMTB, a solid at room temperature, is commonly sold in a mixture. A solvent can be helpful, but not necessary, to dilute TCMTB to be applied to powdered carriers. The following are the preferred characteristics of the solvent: (1) high solvency for TCMTB, (2) low volatility, (3) non-flammability, (4) high flash point, (5) low phytotoxicity, (6) low viscosity, (7) availability, (8) low cost, (9) low odor and (10) absence from the following lists of hazardous substances: (a) SARA 313, (b) CERCLA and (c)

The microbicidal properties of 2-(thiocyanomethylthio)benzothiazole (TCMTB) are well-known. TCMTB has been used for industrial microorganism control for over 20 years. Because of its relative insolubility in water, TCMTB has been formulated mainly as an emulsifiable concentrate or as a water-based product. Such formulations can aid the dispersion of TCMTB in aqueous systems. However, prior to the present invention, it is believed that TCMTB had never been formulated in a powdered form on a solid carrier.

What is proposed in this invention is to apply TCMTB, preferably technical grade TCMTB, directly to a solid carrier, which carrier is preferably inert to the TCMTB. This may be accomplished with or without the use of some amount of solvent and/or emulsifiers as may be tolerated by the application, such as coating or adhesive formulation, intended for the composition of the invention. A solid carrier may preferably be selected from one or more of the carriers mentioned above.

It is possible to select a carrier system that results in very stable formulations of powdered TCMTB. As used herein, stability is measured by assessing how much TCMTB is lost after 30 days at 50° C. A stable formulation, by this standard, is considered to be one which loses no more than 11–12% by weight of the TCMTB from the carrier during the 30 day test. As discussed below, this has been confirmed by TCMTB analysis upon storage and also by efficacy tests of the TCMTB powder. These tests have been carried out on a number of substrates including caulking compounds, latex paints, etc.

A first embodiment of the present invention overcomes the problems and disadvantages of the prior art by providing a composition comprising TCMTB and a solid carrier, wherein the composition is in a powdered form. The carrier, which is itself in powdered form, may be a granule or a dust.

The composition preferably comprises TCMTB in an amount ranging from 0.1% to 60% by weight based on the total weight of said composition. More preferably, the amount ranges from 1 to 40%, even more preferably from 5 to 30% by weight and most preferably from 20 to 30% by weight.

Substantially all of the powder in the TCMTB/carrier powdered composition preferably has a particle size of less than 100 microns. Preferably, more than 80% of said powder has a particle size of less than 20 microns.

The carrier in the powdered composition of the invention is preferably selected from diatomaceous earth, precipitated silica, talc, kaolin, bentonite and attapulgite, and preferably further comprises a wetting agent, a dispersing agent, an anti-caking agent, an antifoaming agent and/or an emulsifier.

Another embodiment of the present invention comprises a method of making a composition comprising TCMTB and a solid carrier, wherein the composition is in a powdered form which comprises mixing TCMTB with the carrier. The TCMTB is preferably dissolved in at least one solvent prior to mixing with the carrier. The solvent is preferably selected from oxygenated solvents, amides, aromatics, aliphatics and paraffinics, naphthenes, animal or vegetable oils, esters, oleic acid, tetrahydrofurfuryl alcohol, dimethyl formamide, N-methyl 2-pyrrolidone and mixtures thereof.

Another embodiment of the present invention comprises a method of preventing the growth of a microorganism on a surface by treating the surface with an effective amount of composition comprising TCMTB and a solid carrier, wherein the composition is in a powdered form. The surface is preferably selected from plastics, adhesives, paints, wood, leather, textiles and building materials, and the microorganism is preferably selected from fungi and bacteria. The surface may also be cutaneous.

Another embodiment of the present invention comprises a method of preventing the growth of a microorganism comprising treating a medium capable of supporting the growth of the microorganism with an effective amount of a composition comprising TCMTB and a solid carrier, wherein the composition is in a powdered form. The medium is preferably selected from plastics, adhesives, caulking compounds, grout and paint, and the microorganism is preferably selected from fungi and bacteria.

The objects and advantages of the invention will be set forth in part in the description that follows, and in part will be obvious from the description, or may be learned by practice of the invention. The objects and advantages of the invention may be realized and attained by means of the instrumentalities and combinations particularly pointed out in the appended claims.

Reference will now be made in detail to the present preferred embodiments of the invention. In the examples and throughout the specification and claims, all parts and percentages are by weight unless otherwise specified.

The present invention is applicable to the preparation of compositions comprising TCMTB and a solid, preferably inert, carrier, wherein the compositions are in a powdered form with desired particle sizes for particular applications and formulations. Generally, such compositions of powdered TCMTB encompass particle sizes of 4 mesh or finer (4750 microns or smaller). In particular, compositions encompassing powders of a size ranging from 4 to 80 mesh (4750–180 microns) can be called granules and those finer than 80 mesh (180 microns) can be called dusts. A preferred particle size of a dust composition is at least 85% finer than a 325 mesh (45 microns).

The particle size of the powdered TCMTB according to the present invention is preferably less than 100 microns. More preferably, more than 80% of the particles are smaller than 20 microns, especially when the composition of the present invention is to be used in adhesive, paint, wood, leather, textile, and building material preservation. If desired, larger particles can be used in accordance with the present invention to prevent the composition from being blown away by wind or for any other reason related to the ultimate application of the composition.

The carriers useful in the powdered TCMTB composition of the invention can be the materials mentioned above. Further examples of carriers which may be used in the present invention include the powders listed in the book *Pesticide Formulation*, edited by Wade Van Valkenburg, published by Marcel Dekker, Inc. (Van Valkenburg, Wade, ed. New York: Marcel Dekker, Inc., 1973) New York 1973, which is specifically incorporated by reference herein. In particular, it is preferred to use diatomaceous earth, precipitated silica, talc, kaolin, bentonite, and attapulgite as carriers.

TCMTB is well-known, is commercially available, for example, as 60% TCMTB, from, for example, Buckman Laboratories, Inc., and can also be synthesized by methods well-known to those skilled in the art. TCMTB is known to be useful in controlling bacteria and fungi in various aqueous systems. The preparation and use of 2-(thiocyanomethylthio)-benzothiazole as a microbicide and a preservative is described in U.S. Pat. Nos. 3,520,976, 4,293,559, 4,866,081, 4,595,691, 4,944,892, 4,839,373, and 4,479,961 give examples of microbicidal properties of 2-(thiocyanomethylthio)benzothiazole. The disclosures of all of these patents are incorporated herein by reference.

2-(Thiocyano-methylthio)benzothiazole is known to be compatible with soluble oil, semi-synthetic and synthetic metalworking fluids. 2-(Thiocyanomethylthio)-benzothiazole is manufactured as aqueous formulations of TCMTB by Buckman Laboratories International, Inc., and sold as Busan® 30WB, Busan® 1030, and Busan® 1118 products.

In applying the TCMTB to a carrier, the general method of pre-blending, coating and post-blending referred to above, or variations thereof that will be apparent to one skilled in the art, can be used. The following procedures are preferably utilized to make the composition of the invention. Procedures for forming powdered TCMTB of dust particle sizes are set forth herein, but it should be understood that similar procedures may be used to form powdered TCMTB of granular particle sizes. However, in order to form powdered TCMTB of granular particle sizes, a carrier of granule particle size is used instead of a carrier of dust particle size.

First, carrier powders are preferably mixed in a Ribbon blender to achieve the desired ratio of powders, if more than one type or size of carrier powder is used. An appropriate mixture of powders is selected based upon such factors as the cost of the powders and desired characteristics of the composition of the invention.

The carriers are preferably free flowable and resist caking. They also preferably have a high adsorption capacity for the TCMTB.

Next, a surface-coating apparatus such as fluid bed, V-blender or other suitable powder coating apparatus can be preferably used for applying, such as by coating, TCMTB, with or without a solvent, to the carrier powder.

A Turbulizer ™ apparatus or a Turbulator ™ apparatus can be used as the powder coating apparatus. The Turbulizer ™ apparatus is manufactured by the Bepex Corporation of Minneapolis, Minn. The use of the Turbulizer ™ apparatus is described in more detail in U.S. Pat. No. 5,043,090, the disclosure of which is incorporated herein by reference. The Turbulator ™ apparatus is manufactured by Ferro-Tech of Wyandotte, Mich.

The paddle setting of Turbulizer ™ apparatus can be: four forward, five flat, and one backward. The rotor speed can be set at various speeds, including 1800 rpm. The Turbulizer ™ apparatus can be operated at room temperature without a cooling jacket. If desired, further processing can be conducted in the Turbulizer ™ apparatus at a high rotor speed (3600 rpm) to reduce the particle size, i.e. de-agglomerate, the powder.

If it is desirable to reduce the particle size further, a hammer mill or pulverizer can also be utilized. Depending upon the particle size desired, the pulverizer can be installed with a one-to-three beater with 1/16 inch plate with mill speed up to 7200 rpm, and the classifier can be set at 4500 rpm or higher. One skilled in the art can routinely select mixing times and settings to achieve desired results, such as homogeneity of the powdered TCMTB composition of the present invention.

Moreover, in applying the TCMTB to the carrier, a solvent for the TCMTB may be used. In the prior art TCMTB EC formulations, amounts of solvent ranging from 50–60% by weight of the total formulation have often been used.

In contrast, in the powdered TCMTB compositions of the present invention, the amount of solvent, if used, preferably is not greater than 10% by weight of the composition of the invention. If a solvent is used, the solvent can be any TCMTB compatible solvent, such as:

(1) oxygenated solvents: diethylene glycol monoethylether, diethylene glycol monomethylether, diethylene glycol monobutylether, hexylene glycol, alkyl acetate, such as EXXATE ™ 600, 700, 800, 900, 1000 or 1300 product, isophorone and propylene glycol;

(2) amide products from the reaction of tall oil, soya oil, palm oil coconut oil cotton seed oil, sunflower oil, safflower oil, and peanut oil with dimethylamine;

(3) aromatics (xylenes, alkylbenzene derivatives);

(4) aliphatics and paraffinics: mineral oil, mineral seal oil;

(5) cycloparaffin;

(6) animal or vegetable oils;

(7) esters: methyl oleate, butyl oleate, glyceryl monooleate, methyl tallowate, methyl soyate;

(8) miscellaneous: oleic acid, tetrahydrofurfuryl alcohol, dimethyl formamide, alkyl alcohol, such as Texanol ™ alcohol, and N-methyl 2-pyrrollidone; and (9) mixtures of any two or more of the above-mentioned solvents.

Particularly preferred solvents include dipropyleneglycol monomethylether, mineral oil, tetrahydrofurfuryl alcohol and natural oils such as Castor oil, since these solvents possess the desirable characteristics noted above.

The concentration of TCMTB in the composition of the present invention is preferably from 0.1% to 60% by weight, more preferably 1% to 40% by weight, and even more preferably 5% to 30% by weight, and most preferably 20% to 30% by weight, based on the total weight of the powdered TCMTB composition.

According to the invention, one can obtain a homogeneous TCMTB powder composition, i.e., the TCMTB is evenly spread over the surface of the carrier. The Stability of TCMTB powder under alkaline conditions can be greatly improved compared with that of the emulsifiable TCMTB concentrate, thereby resulting in better biological efficacy. The exact reason is not clear, but may be related to the following factors: (1) slower release of TCMTB from powder; (2) protection by the powder against alkaline degradation of TCMTB, improving the stability of TCMTB; and (3) more even distribution of TCMTB over larger areas due to the small powder particles which prevent the coalescence of TCMTB. This last factor can be particularly important in paint, adhesive, and construction materials applications of TCMTB.

The composition comprising TCMTB and a solid, preferably inert, carrier in powdered form may also be used to prevent the growth of a microorganism on a cutaneous surface. For example, the composition could be mixed with petroleum jelly and a surfactant to treat athlete's foot. The surfactant can be added to make the petroleum jelly more easily removable.

Representative applications that can be envisioned for the composition of the present invention include use in caulks, sealants, putty, wall paper paste, glues, paint, tannery paste, grout, adhesives, such as vinyl acetate wallcovering adhesives, asbestos tile, paper coating, soap wrap, PVC products, such as shower curtains, refrigerator gaskets, and athletic shoes, textiles, seed treatment, foliar fungicide, veterinary uses, coatings electrostatically applied to metals, pigment and dye preservation, and cutaneous antifungal agents (used for human skin fungus control, such as treatment of athlete's foot).

Amounts of the powdered TCMTB composition of the present invention will be apparent to those skilled in the art and can be readily determined for particular applications. For example, for the preservation of caulking-sealants and wallcovering adhesives, the powdered TCMTB composition of the present invention can preferably be used at rates of 0.45% to 2.25% based on the total wet weight of the product to be protected.

EXAMPLE 1

155 pounds of Sipernat 22 S solid carrier (silica-based Degussa Corp. product, having a pH of 6.3, an average particle size of 6.3 microns, a DBP absorption of 270%, a BET surface area of 190 $m^2/g$, a tapped density of 120 g/l, and an average agglomerate size of 7 microns) and 95 pounds of Celite 110 (described below) solid carrier were mixed in a Ribbon Blender for 20 minutes. The resulting powder was fed using an Accrison Feeder at 660 pounds per hour, and 60% active TCMTB in dipropylene glycol monomethyl ether solvent was fed with a Piston Pump Package at 340 pounds per hour to a Turbulizer ™ (Model TC8) apparatus at a rotor speed of 1800 rpm. 86% of the product passed 38 microns after the first run, and over 90% passed 38 microns after a second run through the Turbulizer ™ apparatus at 3600 rpm. TCMTB was introduced into the apparatus during the first run only. The product contained 20% by weight TCMTB. A stability analysis of the product is set forth below in Table 1.

EXAMPLE 2

155 pounds of Sipernat 22 (silica-based Degussa Corp. product having a pH of 6.3, a DBP absorption of 260%, a BET surface area of 190 $m^2/g$, a tapped density of 270 g/l, and an average agglomerate size of 100 microns) solid carrier and 95 pounds of Celite 110 (described below) solid carrier were mixed in a Ribbon blender for 20 minutes. This powder was fed with Accrison Feeder at 660 pounds per hour, and 60% active TCMTB in dipropylene glycol monomethyl ether solvent was fed with a Piston Pump Package at 340 pounds per hour to a Turbulizer ™ (Model TC8) apparatus at a rotor speed of 1800 rpm. Over 60% of the product passed 38 microns. This product was then processed with a Pulvocron ™ (Model PC 20) pulverizer with one beater plate on the mill at a mill speed of 6230 rpm. The classifier rpm was 4500. The feed rate was 257 pounds per hour and the process was conducted at ambient temperature. Products were collected by means of a baghouse with a 273 sq. ft. bag area and an exhaust fan. The mean particle size of the product was 10.5 microns. This product had 20% TCMTB by weight. A stability analysis of the product is set forth below in Table 1.

TABLE 1

| Stability Analysis of TCMTB Content in Examples 1-2 | | | | | | | | | | |
|---|---|---|---|---|---|---|---|---|---|---|
| | | 30 days | | | 45 days | | | 60 days | | |
| | Original | 4° C. | RT | 50° C. | 4° C. | RT | 50° C. | 4° C. | RT | 50 |
| Ex. 1: | 19.9% | 20.6 | 20.7 | 20.1 | 20.2 | 20.8 | 19.6 | 20.4 | 20.8 | 19 |
| Ex. 2: | 20.6% | 21.3 | 21.2 | 19.2 | 20.9 | 20.6 | 18.7 | 21.3 | 21.2 | 19 |

EXAMPLE 3

The products from Example 1 or Example 2 were mixed (postblended) with talc at a one-to-one weight ratio in a Ribbon blender to form a homogeneous blend.

EXAMPLE 4

Sipernat 22 S carrier in Example 1 was replaced with Sipernat 22 ns (described below) solid carrier, which has a smaller particle size than Sipernat 22 S.

EXAMPLE 5

Sipernat 22 LS in Example 4 was replaced with Cab-O-Sil M-5 (described below) solid carrier.

EXAMPLE 6

Cab-0-Sil M-5 was the only powder used as a solid carrier, and a solution of TCMTB 80% active was used to replace the 60% TCMTB in Example 1. The weight ratio of powder to liquid is 62 to 38. This process was used to make an approximately 30% TCMTB powder as a final product.

| CHARACTERISTICS OF CARRIERS USED IN EXAMPLES | | | | | | |
|---|---|---|---|---|---|---|
| | Oil absorption | pH | Diam. (microns) | Manuf. | Spec Grav | |
| Cab-O-Sil M-5 | 300 | 3.8 | 0.014 | Cabot | 2.2 | Amorphous - Synthetic Silica |
| Sipernat 22LS | 240 | 5.5–7.0 | 3.5 | Degussa | 2.1 | Amorphous - Synthetic Silica |
| Celite 110 | 130 | 9.1 | 9 | Manville | 2.3 | Diatomaceous |
| Celite 266 | 135 | 6.0 | 2.0 | Manville | 2.1 | Diatomaceous |
| Zeolex 7 | 115 | 7.0 | 6 | Huber | 2.1 | Precipitated Amorphous Silicate Na Aluminosilicate |
| Syloid 221 | 275 | 7.0 | 7 | Davison | 2.01 | Amorphous Synthetic Silica |
| Syloid 235 | 275 | 4.0 | 4 | Davison | 2.01 | Amorphous Synthetic Silica |

EXAMPLE 7

Celite 110 solid carrier was used to replace CAB-0-SIL M-5 in Example 6.

EXAMPLE 8

Celite 266 (described below) solid carrier was used to replace Celite 110 in Example 7.

EXAMPLE 9

ZEOLEX 7 (described below) solid carrier (sodium aluminosilicate, manufactured by J. M. Huber Corp.) was used to replace Celite 266 in Example 8.

EXAMPLE 10

China clay can be used to replace talc in Example 3.

EXAMPLE 11

Bentonite can be used to replace talc in Example 3.

EXAMPLE 12

Corn starch can be used to replace talc in Example 3.

EXAMPLE 13 a-g

Powdered 30% TCMTB on solid powder compositions in accordance with the present invention were prepared having the following components: (a) 62% Syloid 221 (described below) carrier and 38% of 80% TCMTB; (b) 62% Syloid 235 (described below) carrier and 38% of 80% TCMTB; (c) 62% Cab-o-Sil M-5 carrier and 38% of 80% TCMTB; (d) 62% Sipernat 22 LS carrier and 38% of 80% TCMTB; (e) 62% Celite 110 carrier and 38% of 80% TCMTB; (f) 62% Celite 266 carrier and 38% of 80% TCMTB and (9) 62% Zeolex 7 carrier and 38% of 80% TCMTB A stability. analysis of the each product 13 a-9 is set forth below in Table 2.

TABLE 2

Stability Analysis of TCMTB Content in Examples 13 a-g

| Example | Initial | 31 days (50° C.) | 45 days (50° C.) | 60 days |
|---|---|---|---|---|
| 13a | (i) 26.0% (ii) 26.9% | 21.92% | 21.0% | 20.0 |
| 13b | 31.0% | 30.04% | 29.0% | 27.0 |
| 13c | 32.2% | 32.45% | 32.6% | 31.9 |
| 13d | 31.5% | 28.34% | 28.3% | 27.5 |
| 13e | 30.0% | 30.24% | 30.2% | 30.6 |
| 13f | 31.1% | 30.30% | 29.9% | 30.2 |
| 13g | | 91.7% | | |

TABLE 2-continued

Stability Analysis of TCMTB Content in Examples 13 a-g

| Example | Initial | 31 days (50° C.) | 45 days (50° C.) | 60 days |
|---|---|---|---|---|
| | | | | of original |

Evaluation of the Effectiveness of Powdered TCMTB

The purpose of this study was to evaluate TCMTB powder as a fungicidal agent in water-based adhesives and sealants. The powdered TCMTB product of each of Example 13g above was evaluated at 0.5, 0.75, 1.0, and 1.5% powdered TCMTB product, based on the combined weight of the powdered TCMTB product and the adhesive or sealant, along with liquid Busan ® 1030, a product containing 30% by weight TCMTB and stabilizers and solvents, at the same levels for comparison.

The test materials were applied over gypsum wallboard panels, allowed to air dry for a minimum of five days, and then tested for fungal resistance capabilities.

This test was conducted according to ASTMD-3273-82, which covers the evaluation of a material's resistance to the growth of mold that might occur on its surface in a severe mold environment. The testing device was an environmental chamber kept at a constant temperature of 90±2° F. and a relative humidity of 95 to 98%. Within the chamber are dirt boxes containing soil inoculated with *Aspergillus niger*, *Aspergillus oryzae*, and an unknown species of *Penicillium*.

The test materials were hung vertically, with the bottom of the test material being approximately three inches above the surface of the inoculated soil and with sufficient spacing to allow circulation of air and to prevent contact both between samples and between the samples and the wall surfaces.

The test materials were exposed in the environmental chamber for approximately five weeks. The test samples were evaluated according to ASTMD-3274 against photographic reference standards that provide a numerical basis for rating the degree of fungal growth or soil and dirt accumulation on paint films.

The samples were evaluated on a scale of zero to ten, with ten indicating an absence of mold growth. A rating of nine or eight signifies a very slight to slight amount of mold growth. A rating of seven or six denotes a slight to medium amount of mold growth. A rating of six signifies marginal protection. Ratings of five or below indicate failure. The following table records the mold resistance ratings obtained. The results of the TCMTB powder products at each level was essentially the same, as reported in the following Table.

TABLE

| Sample I.D. | Water Based Adhesives | Water Based Sealants |
| --- | --- | --- |
| Control (0.0%) | 4 | 0 |
| 0.50% TCMTB Powder | 10 | 10 |
| 0.75% TCMTB Powder | 10 | 10 |
| 1.0% TCMTB Powder | 10 | 10 |
| 1.5% TCMTB Powder | 10 | 10 |
| 0.50% Busan 1030 | 9 | 9 |
| 0.75% Busan 1030 | 10 | 10 |
| 1.0% Busan 1030 | 10 | 10 |
| 1.5% Busan 1030 | 10 | 10 |

Base formulations for the above-mentioned adhesives and sealants were as follows.

| Vinyl Wallpaper Adhesive | |
| --- | --- |
| Ingredients | lbs/100 gallons |
| Water | 337.3 |
| HEC-QP-52000 hydroxyethylcellulose thickener | 12.2 |
| Diethylene glycol | 40.6 |
| Butyl cellosolve | 22.3 |
| ASP-400 alumino-silicate clay | 146.0 |
| UCAR Latex 163 Polymer Binder | 380.3 |
| | 938.7 |

| Sealant | |
| --- | --- |
| Ingredients | lbs/100 gallons |
| UCAR Latex 163 Polymer | 417.25 |
| Triton X-405 Surfactant | 8.75 |
| Benzoflex 9-88 Plasticizer | 109.75 |
| Varsol #1 Solvent | 25.00 |
| Water | 18.75 |
| Ethylene glycol | 12.50 |
| Calgon T postassium phosphate dispersion agent | 12.50 |
| Atomite calcium carbonate pigment filler | 600.00 |
| Barytes #1 barium sulfate filler | 37.50 |
| Ti-Pure R-900 titanium dioxide pigment | 10.00 |
| | 1252.00 |

Evaluation of the Effectiveness of Powdered TCMTB in Adhesives and Caulk-Sealants In-container multiple challenge preservation tests involving each of the powdered TCMTB products of Example 13g above was above were performed upon a resin acetate wallcovering adhesive (Coltire ™ adhesive) and a caulking-sealant (Baysilane 400 ™ product available from Mobay Chemical) which had not previously had preservatives added to them. The challenge microorganisms were a mixture of the following: *Enterobacter aerogens*, ATCC #13048; *Pseudomonas aeruginosa*, ATCC #15442; and *Aspergillus niger*, ATCC #6275. The bacteria, *E. aerogenes* and *P. aeruginosa* were precultured in the adhesive caulking-sealant materials so that these materials would not shock adapted microorganisms. The fungus, *A. niger*, was likewise precultured in these materials for the same reason. All microorganisms were observed to grow and proliferate well in these materials prior to testing. Each bacterial species was added to a 50 ml solution of the respective materials in order to produce a final concentration of approximately $1 \times 10^6$ colony-forming units (CFU) per ml of material. The fungal species was added in a similar manner to these materials in order to produce a final concentration of approximately $1 \times 10^4$ colony-forming units (CFU) per ml of material. This microbial challenge was repeated once every seven days for three weeks following the plating recovery of the previous week's challenge in order to culture for microbial survivors. Plating media consisted of nutrient agar (NA) for bacterial species and acidified mycophil agar (AMA) for the fungal species. Plating was performed using a sterile swab technique. Bacterial plates were then cultured at 32° C. for 72 hours and fungal plates were cultured at 28° C. for 14 days.

The following standard was used to evaluate the results:

| | |
| --- | --- |
| 0 colony forming units (cfu)/plate = | (−) for excellent control |
| 1 or more (cfu)/plate = | (+) for survivor growth. |

The results for the powdered TCMTB product was as reported immediately below.

HEAT STABLE TCMTB DRY POWDER AS A PRESERVATIVE FOR CAULKING SEALANTS AND RESIN ADHESIVES (IN-CONTAINER MULTIPLE CHALLENGE)

| Sample | TCMTB (%) | | | | | | |
| --- | --- | --- | --- | --- | --- | --- | --- |
| | 0.0 | 0.025 | 0.050 | 0.100 | 0.200 | 0.500 | |
| caulk-sealant | + | − | − | − | − | − | WEEK 1 |
| | + | − | − | − | − | − | WEEK 2 |
| | + | + | − | − | − | − | WEEK 3 |
| | + | + | − | − | − | − | WEEK 4 |
| resin adhesive | + | − | − | − | − | − | WEEK 1 |
| | + | − | − | − | − | − | WEEK 2 |
| | + | + | − | − | − | − | WEEK 3 |
| | + | + | − | − | − | − | WEEK 4 |

No sign of bacterial or fungal survivors was found even at the lowest preservative level after a month with three subsequent challenges. Efficacy was indicated for each of the powdered TCMTB samples at 0.05% and above.

HEAT STABLE TCMTB DRY POWDER AS A PRESERVATIVE FOR CAULKING SEALANTS AND RESIN ADHESIVES (TROPICAL CHAMBER CHALLENGE)

Caulk-sealant and resin adhesive were applied to regular wallboard (4"×2") pieces. Various concentrations of the powdered TCMTB products of Examples 13g was added to the sealant and adhesive materials prior to application along with a control which had no added preservative. All wallboard pieces were in turn placed in a tropical chamber where numerous species of bacterial and fungi inhabited the soil. Humidity within the chamber was between 95 and 100%. All wallboard pieces remained in the chamber for four weeks and were examined each week for preservative failure as evidenced by growth of bacteria and/or fungi upon the surface of the treated wallboard. Sample pieces were scored on a growth/no growth basis.

Growth=(+); No Growth=(−)

The results for each of the powdered TCMTB product was as reported immediately below.

TROPICAL CHAMBER RESULTS
OF WALLBOARD TREATMENTS

| Sample | TCMTB (%) | | | | | | |
|---|---|---|---|---|---|---|---|
| | 0.0 | 0.025 | 0.050 | 0.100 | 0.200 | 0.500 | |
| caulk-sealant | + | + | − | − | − | − | WEEK 1 |
| | + | + | − | − | − | − | WEEK 2 |
| | + | + | + | − | − | − | WEEK 3 |
| | + | + | + | − | − | − | WEEK 4 |
| resin adhesive | + | + | − | − | − | − | WEEK 1 |
| | + | + | − | − | − | − | WEEK 2 |
| | + | + | + | − | − | − | WEEK 3 |
| | + | + | + | − | − | − | WEEK 4 |

Tropical chamber tests showed that a concentration of 0.100% and above for each of the powdered TCMTB products tested preserved both the sealant and the adhesive after a month.

Evaluation of Powdered TCMTB in Paints

The fungicidal capabilities of the powdered TCMTB products of Example 13g above was evaluated in an alkyd modified, acrylic latex paint. The usage levels are recorded on the attached data tables.

The paints were exposed in an environmental chamber for fungal resistance evaluation. The paints were brush applied, two coats, over gypsum wallboard panels and exposed in the chamber after sufficient drying, a minimum of 24 hours. The test was done according at ASTMD-3273-82, which covers the evaluation of a paint's resistance to the growth of mold that might occur on its surface in a severe mold environment. The testing device was an environmental chamber kept at a constant temperature of 90°±2° F. and a relative humidity of 95 to 98%. Within the chamber are dirt boxes containing soil inoculated with the following known organisms: *Aspergillus niger, Aspergillus oryzae,* and an unknown species of *Penicillium.*

The painted panels were hung vertically with the bottom approximately three inches above the surface of the inoculated soil and with sufficient spacing to allow circulation of air and to prevent contact between samples or with wall surfaces.

The test panels were exposed in the chamber for four weeks. The panels were evaluated according to ASTMD-3274-82, which are photographic reference standards that provide a numerical basis for rating the degree of fungal growth or soil and dirt accumulation on paint films. The samples were evaluated on a scale of zero to ten, with ten indicating an absence of mold growth. A rating of nine or an eight signifies a very slight to a slight amount of mold growth. A rating of seven or six denotes a slight to a medium amount of mold growth. A rating of six signifies marginal protection. Ratings of five or below indicate failure. The Table immediately below records the data obtained from these experiments. The results for the TCMTB powdered products of Example 13g was essentially the same.

TABLE

| Sample I.D. | Mold Resistance Rating | |
|---|---|---|
| | Panel 1 | Panel 2 |
| Control (0.0%) | 0 | 0 |
| 0.3% TCMTB Powder | 8 | 9 |
| 0.6% TCMTB Powder | 9 | 9 |

The test paints were also evaluated for fungal resistance using the ASTMG21 method that determines the resistance of synthetic polymeric materials to fungi. This method has been adapted for the evaluation of paints.

The paints were brushed, one coat, over both sides of sterile filter paper. The painted filter paper was allowed to air dry a minimum of 24 hours before testing began. One inch squares were cut from each painted filter paper and placed onto potato dextrose agar in sterile petri plates. The surface of the painted filter paper was inoculated with one milliliter of a fungal suspension of *Aspergillus niger.* The agar plates were gently rotated to distribute the inoculum over the entire plate, after which they were placed in an incubator at a temperature of 30° C. The plates were exposed for 21 days and then rated for fungal growth.

The Table immediately below records the data obtained. The results for each of the powdered TCMTB products of Example 13g essentially the same.

TABLE

| Sample I.D. | Observed Plate 1 | Growth Plate 2 | Rating Plate 3 |
|---|---|---|---|
| Control (0.0%) | 4 | 4 | 4 |
| 0.3% TCMTB Powder | 1 | 1 | 2 |
| 0.6% TCMTB Powder | 1 | 0 | 0 |

*Zones of inhibition noted

Key:
| | |
|---|---|
| None | 0 |
| Traces of growth (<10%) | 1 |
| Light growth (10 to 30%) | 2 |
| Medium growth (30 to 60%) | 3 |
| Heavy growth (60% to complete coverage) | 4 |

Pink Stain Test

Sheets of flexible PVC containing the powdered TCMTB composition of Example 1 (BL 1222) and a control without preservative were evaluated for resistance against the pink staining organism *Streptoverticillian Reticilliua.*

One inch squares of the PVC were placed onto solid yeast malt extract agar and then inoculated with 1.0 ml of a suspension of the test organism. The plates were gently rotated to evenly distribute the inoculum over the agar surface. The plates were incubated at 30° C. for 21 days. The following ratings were obtained:

| Sample I.D. | Rating | |
|---|---|---|
| Control | TS | −1 |
| Control | TS | −1 |
| Control | SS | −2 |
| BL-1222 | NS | −0 |
| BL-1222 | NS | −0 |
| BL-1222 | NS | −0 |

Key:
| | | |
|---|---|---|
| NS | No stain | −0 |
| TS | less than 10% | −1 |
| SS | 10 to 30% coverage | −2 |
| MS | 30 to 60% coverage | −3 |
| HS | 60% complete coverage | −4 |

HEAT STABLE TCMTB DRY POWDER AS A PRESERVATIVE FOR CAULKING SEALANTS AND RESIN ADHESIVES (IN-CONTAINER MULTIPLE CHALLENGE)

In-container multiple challenge preservation tests involving the powdered TCMTB products of Example 13g above was performed upon a resin acetate wallcovering adhesive and a caulking-sealant which had not previously had preservatives added to them. The challenge microorganisms were a mixture of the following: *Enterobacter aerogenes*, ATCC #13048; *Pseudomonas aeruqinosa*, ATCC #15442; and *Aspergillus niger*, ATCC 36275. The bacteria, *E. aerogenes* and *P. aeruginosa* were precultured in the adhesive and caulking-sealant materials in order that these materials would not shock unadapted microorganisms. The fungus, *A. niger* was likewise precultured in these materials for the same reason. All microorganisms were observed to grow and proliferate well in these materials prior to testing challenge with added preservative. Each bacterial species was added to a 50ml solution of the respective materials in order to produce a final concentration of approximately $1 \times 10^6$ colony forming units (CEU) per ml of material. The fungal species was added to a similar quantity of these materials in order to produce a final concentration of approximately $1 \times 10^4$ colony forming units (CFU) per ml of material. This microbial challenge was repeated once every seven days for three weeks following the plating for the previous week's challenge in order to culture for microbial survivors. Plating media consisted of Nutrient Agar (NA) for bacterial species and Acidified Mycophil Agar for the fungal species. Plating was performed by using a sterile swab technique. Bacterial plates were then cultured at 32 C for 72 hours and fungal plates were cultured at 28 C for 14 days. The following was the scoring procedure for results: 0 colony forming units (cfu)/plate = excellent control:Score (−) 1 or more cfu/plate = Score (+) for survivor growth The results of the powdered TCMTB product was as reported immediately below.

| TCMTB DRY POWDER AS A PRESERVATIVE FOR CAULKING-SEALANTS AND RESIN ADHESIVES | | | | | | | |
|---|---|---|---|---|---|---|---|
| | TCMTB (%) | | | | | | |
| Sample Description | 0 | 0.05 | 0.10 | 0.50 | 1.0 | 2.0 | |
| Clear caulk-sealant | + | − | − | − | − | − | week 1 |
| | + | − | − | − | − | − | week 2 |
| | + | − | − | − | − | − | week 3 |
| | + | − | − | − | − | − | week 4 |
| Resin adhesive | + | − | − | − | − | − | week 1 |
| | + | − | − | − | − | − | week 2 |
| | + | − | − | − | − | − | week 3 |
| | + | − | − | − | − | − | week 4 |

There was no sign of bacterial or fungal survivors even at the lowest preservative level after a month with three subsequent challenges. Efficacy was indicated for each of the powdered TCMTB samples at all preservative levels.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A stable powder composition comprising TCMTB adsorbed onto a solid carrier selected from diatomaceous earth, precipitated silica, talc, kaolin, bentonite, and attapulgite or a mixture thereof, wherein the composition is in a powdered form, the solid carrier has acidic or neutral pH, and the composition loses no more than 11–12% by weight of the TCMTB from the solid carrier over 30 days at 50° C.

2. The composition of claim 1, wherein said composition is a dust.

3. The composition of claim 1, wherein said composition comprises TCMTB in an amount ranging from 0.1% to 60% by weight based on the total weight of said composition.

4. The composition of claim 3, wherein said amount of TCMTB ranges from 1 to 40%.

5. The composition of claim 4, wherein said amount of TCMTB ranges from 5 to 30% by weight.

6. The composition of claim 2, wherein said dust has a particle size of less than 100 microns.

7. The composition of claim 2, wherein more than 80% of said dust has a particle size of less than 20 microns.

8. The composition of claim 1, further comprising a wetting agent.

9. The composition of claim 1, further comprising a dispersing agent.

10. The composition of claim 1, further comprising an anti-caking agent.

11. The composition of claim 1, further comprising an antifoaming agent.

12. The composition of claim 1, further comprising an emulsifier.

13. The composition of claim 1, wherein said composition is in granular form.

14. The composition of claim 1, wherein the carrier has an oil adsorptivity of at least 115.

15. A method of preventing the growth of a microorganism on a surface, comprising treating said surface with an effective amount of a composition comprising TCMTB adsorbed onto a solid carrier selected from diatomaceous earth, precipitated silica, talc, kaolin, bentonite, and attapulgite or a mixture thereof, wherein the composition is in a powdered form, the solid carrier has acidic or neutral pH, and the composition loses no more than 11–12% by weight of the TCMTB from the solid carrier over 30 days at 50° C.

16. The method of claim 15, wherein said surface is selected from plastics, adhesives, paints, wood, leather, textiles and building materials.

17. The method of claim 15, wherein said microorganism is selected from fungi and bacteria.

18. The method of claim 15, wherein said surface is cutaneous.

19. The method of claim 15 wherein said composition is a dust.

20. The method of claim 15, wherein said composition is in granular form.

21. A method of preventing the growth of a microorganism, comprising treating a medium capable of supporting the growth of said microorganism with an effective amount of a composition comprising TCMTB adsorbed onto a solid carrier selected from diatomaceous earth, precipitated silica, talc, kaolin, bentonite, and attapulgite or a mixture thereof, wherein the composition is in a powdered form, the solid carrier has acidic or neutral pH, and the composition loses no more than 11–12% by weight of the TCMTB from the solid carrier over 30 days at 50° C.

22. The method of claim 21, wherein said medium is selected from plastics, adhesives, caulking compounds, grout and paint.

23. The method of claim 21, wherein said microorganism is selected from fungi and bacteria.

24. The method of claim 21, wherein said composition is a dust.

25. The method of claim 21, wherein said composition is in granular form.

26. The composition of claim 1, wherein said TCMTB is present in an amount ranging from 20-30% by weight of said composition.

27. The composition of claim 1, wherein said carrier is inert.

28. The method of claim 1, wherein said TCMTB is present in an amount ranging from 20-30% by weight of said composition.

29. The method of claim 1, wherein said carrier is inert.

30. The method of claim 15, wherein said TCMTB is present in an amount ranging from 20-30% by weight of said composition.

31. The method of claim 15, wherein said carrier is inert.

32. The method of claim 15, wherein said composition is stable.

33. The method of claim 21, wherein said TCMTB is present in an amount ranging from 20-30% by weight of said composition.

34. The method of claim 21, wherein said carrier is inert.

35. The composition of claim 1, wherein the carrier is acidic.

36. The composition of claim 4, wherein the carrier is precipitated silica or diatomaceous earth and has an acidic pH.

37. The method of claim 15, wherein the carrier is acidic.

38. The method of claim 15, wherein the carrier is precipitated silica or diatomaceous earth and has an acidic pH.

39. The method of claim 21, wherein the carrier is acidic.

40. The method of claim 21, wherein the carrier is precipitated silica or diatomaceous earth and has an acidic pH.

41. The composition of claim 36, wherein the carrier has an oil adsorptivity of at least 115.

* * * * *